United States Patent [19]

Sollman

[11] 3,941,831
[45] Mar. 2, 1976

[54] RESOLUTION OF ALKYL ESTERS OF DL-PHENYLALANINE

[75] Inventor: Paul B. Sollman, Wilmette, Ill.

[73] Assignee: G. D. Searle & Co., Chicago, Ill.

[22] Filed: Sept. 10, 1973

[21] Appl. No.: 395,940

[52] U.S. Cl............................................ 260/471 A
[51] Int. Cl.²..................................... C07C 103/32
[58] Field of Search............................... 260/471 A

[56] References Cited
UNITED STATES PATENTS
3,734,952  5/1973  Krubiner.......................... 260/471 A OTHER PUBLICATIONS
Greenstein, J. P. *Chemistry of the Amino Acids*, Vol. I (1961), Pub. by John Wiley & Sons, (N.Y.), pp. 715–716.

*Primary Examiner*—Anton H. Sutto
*Assistant Examiner*—L. A. Thaxton
*Attorney, Agent, or Firm*—John A. Dhuey

[57] ABSTRACT

Treatment of DL-phenylalanine alkyl esters with N-acyl-D-phenylalanines results in the formation of insoluble salts of the L-phenylalanine alkyl esters and N-acyl-D-phenylalanines. The salts are isolated and decomposed to afford the desired L-phenylalanine alkyl esters, which are important starting materials in the preparation of artificial sweetening agents.

10 Claims, No Drawings

3,941,831

RESOLUTION OF ALKYL ESTERS OF DL-PHENYLALANINE

BACKGROUND OF THE INVENTION

Lower alkyl esters of L-phenylalanine are preferred starting materials in the manufacture of certain sweetening agents as disclosed in U.S. Pat. No. 3,492,131. However, heretofore those starting materials have been difficult and expensive to obtain. Due to the absence of suitable asymmetric syntheses, prior art efforts have been directed most often to the resolution of the DL-compounds.

Prior art methods have employed resolving agents derived from amino acids different than those being resolved, see for example, Kato and Tsuchiya, *Agr. Bio. Chem.*, Vol. 26, No. 8, 467 and 473 (1962). As an exception, the resolution of the t-butyl ester of DL-phenylalanine employing N-carbobenzoxy-L-phenylalanine as the resolving agent has been reported in *Roczniki. Chem.*, 40 (11/12), 1895 (1966). However, the urethane type carbobenzoxy group employed therein is not desirable because of its potentially dangerous preparation from phosgene and benzyl alcohol. Additonally, from an economic standpoint, it is undesirable to utilize a derivative of L-phenylalanine as resolving agent since its use as starting material for the production of sweetening agents makes it very valuable. Even small losses of resolving agent would result in substantial additional costs.

OBJECTS OF THE INVENTION

It is an object of this invention to provide an economical and facile process for the preparation of the alkyl esters of L-phenylalanine from the alkyl esters of DL-phenylalanine; it is another object of this invention to utilize a derivative of D-phenylalanine, the undesired isomer in the preparation of sweetening agents, as a resolving agent; it is furthermore an object of this invention to utilize appropriate derivatives which may be recycled within the process to minimize overall costs; it is also an object of this invention to utilize materials which will form insoluble salts with the alkyl esters of L-phenylalanine, thus assuring purity of the L-isomer product. The successful achievement of these and other objects of this invention will be apparent from the following description of the invention.

DESCRIPTION OF THE INVENTION

The invention is concerned generally with the resolution of amino acids. More particularly, it is concerned with a new and unobvious process for the resolution of alkyl esters of DL-phenylalanine. Also, it is concerned with the production of certain novel salts of the alkyl esters of L-phenylalanine and N-acyl-D-phenylalanines. Those salts are conveniently represented by the following formula

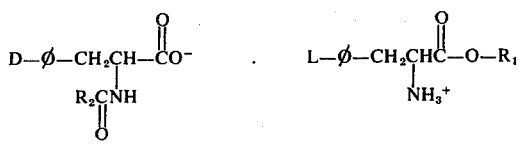

wherein $R_1$ is a lower alkyl radical containing 1–4 carbon atoms inclusive and $R_2$ is hydrogen or a lower alkyl radical containing 1–7 carbon atoms inclusive. The salts are useful intermediates in the preparation of the lower alkyl esters of L-phenylalanine. Illustrative of those alkyl radicals intended are methyl, ethyl, n-propyl, isopropyl, n-butyl, isobutyl, sec-butyl and tert-butyl.

Other art equivalent acyl blocking groups, both aliphatic and aryl, may be utilized for $R_2$, but the lower alkyl radicals described above are preferred.

The instant process is practiced preferably by contacting an alkyl ester of DL-phenylalanine in a suitable solvent, preferably a polar solvent, with an N-acyl-D-phenylalanine; isolating the salt of the corresponding alkyl ester of L-phenylalanine and N-acyl-D-phenylalanine; decomposing the salt into its respective components; and isolating the desired alkyl exter of L-phenylalanine.

The formation of the crystalline D-L salt of N-acyl-D-phenylalanine with the alkyl esters of L-phenylalanine is surprising and unobvious particularly in view of the disclosure in *Roczniki. Chem.*, 40 (11/12), 1895 (1966), of the L-L salt formation of N-carbobenzoxy-L-phenylaianine with the t-butyl ester of L-phenylalanine. The instant salt formation is most advantageous since it permits the N-acyl derivatives of D-phenylalanine to be utilized as the resolving agents, effecting substantial cost savings over the use of the L-isomer. Thus, the desired L-isomer of phenylalanine need not be tied up in the process. Furthermore, the crystallization of the D-L salts affords, upon decomposition and separation, pure product consisting of the appropriate alkyl ester of L-phenylalanine.

The particular combination of an alkyl ester of a DL-amino acid and an acyl blocked optically active D-amino acid resolving agent, which is derived from the same amino acid from which the alkyl ester is derived, results in the selective precipitation of the corresponding salt of the N-acyl-D-amino acid and the L-amino acid alkyl ester. Thus, when the N-acyl derivative of a D-amino acid is contacted with the idential DL-amino acid alkyl ester, the salt of the N-acyl-D-amino acid and the L-amino acid alkyl ester preferentially crystallizes from solution. The naturally occuring amino acids, e.g. aspartic acid, asparagine, glutamine, glutamic acid, alanine, valine, leucine, isoleucine, serine, threonine, methionine, cysteine, cystine, tyrosine, proline, lysine, aginine and ornithine may be resolved in this manner. Also, similar synthetic amino acids may be resolved in the manner described. It is noted that when an N-acyl-L-amino acid resolving agent is employed, there is obtained, preferentially, the salt comprised of the N-acyl-L-amino acid and the alkyl ester of the D-amino acid.

Typically, N-acetyl-D-phenylalanine is allowed to contact DL-phenylalanine methyl ester in a suitable solvent, e.g. methanol or water, to produce a crystalline salt of N-acetyl-D-phenylalanine and L-phenylalanine methyl ester. That salt is separated from the filtrate and decomposed with aqueous hydrochloric acid to afford N-acetyl-D-phenylalanine as a precipitate and L-phenylalanine methyl ester hydrochloride in solution. After filtering, the solvent in the filtrate is removed to afford the hydrochloride salt of L-phenylalanine methyl ester. Alternatively, the salt of N-acetyl-D-phenylalanine and L-phenylalanine methyl ester is dissolved in aqueous potassium carbonate and extracted with ether. The D-amide remains in the aqueous phase and the L-ester remains in the organic phase. After phase separation, the ethereal solution is acidified with hydrochloric acid-isopropanol to precipitate the hydrochloride salt of L-phenylalanine methyl ester.

It is apparent that the starting materials useful in the instant process may be employed as their equivalent salts without affecting the operability of the process. For example, the hydrochloride salt of DL-phenylalanine methyl ester may be utilized along with the sodium salt of N-acyl-D-phenylalanine.

It is understood that once the D-L salt is obtained, standard chemical techniques can be employed to separate the individual components. Decomposition of the salt with aqueous hydrochloric acid is satisfactory. Alternatively, an aqueous solution of the salt may be contacted with a base such as sodium carbonate, then separated and acidified to yield the desired components. Also, the desired L-phenylalanine alkyl esters may conveniently be separated as salts, e.g. hydrochloride salts, when they are oils in their free state, for ease of handling and storage.

In another embodiment of this invention, the particular by-products of the resolution process are recycled, thereby making the process additionally advantageous. The alkyl ester of D-phenylalanine remaining in solution after the separation of the D-amide-L-ester salt can be racemized to afford the DL-ester starting material. This racemization preferably is accomplished with an alkali metal alkoxide in the corresponding lower alkanol solvent. Illustrative of the alkali metals are lithium, sodium and potassium. The lower alkanols intended contain 1–6 carbon atoms and are illustrated by methanol, ethanol and t-butanol. Typical alkoxide groups contain 1–4 carbon atoms and are illustrated by methoxide, ethoxide, t-butoxide and the like. Thus, for example D-phenylalanine methyl ester is refluxed with sodium methoxide in methanol to afford DL-phenylalanine methyl ester. It is not necessary that the reaction be run at the reflux temperature. However, at lower temperatures the racemization takes place at a slower rate. For example, complete racemization of D-phenylalanine methyl ester takes approximately 2 days at room temperature, whereas it is completed in about 2 ½ hours at the reflux temperature. Generally, it is desirable to choose an alkoxide group and a lower alkanol corresponding to the alkyl ester being racemized. It is noted that any L-phenylalanine alkyl ester present will be racemized as well as may be recycled to provide starting DL-ester.

It is apparent also that the N-acyl-D-phenylalanine, recovered from the decomposition of the salt of N-acyl-D-phenylalanine and L-phenylalanine alkyl ester, can be recycled to provide starting resolving agent.

Alternatively, but less preferably, the D-phenylalanine alkyl esters can be hydrolyzed and acylated to provide the N-acyl-D-phenylalanine resolving agent. Since large quantities of the N-acyl derivatives are not lost in the process, only a portion of the N-acyl derivatives produced by this alternate process would likely be utilized. Thus, the N-acyl-D-phenylalanines can also be racemized to the DL-derivatives corresponding, they hydrolyzed and esterified to provide additional amounts of DL-phenylalanine alkyl ester.

A further and particularly unobvious advantage of the process is manifested by the unexpected purity of the salt of the D-amide-L-ester obtained when water is utilized as the solvent medium during salt formation. Initial salt obtained from the reaction mixture is of such purity that it need not be recrystallized further and can be decomposed immediately to obtain the desired L-phenylalanine alkyl ester.

Reaction conditions for the practice of the instant invention will be apparent to those skilled in the art of chemical manufacturing procedures. Temperatures, solvents and reaction times are not critical to the instant process and may be chosen according to standard chemical manufacturing techniques. However, polar solvents, e.g. water, lower alkanols such as methanol, ethanol and t-butanol, and equivalent solvents, have been found preferable for D-L salt formation. Generally, salt formation occurs at room temperatures, but is not limited thereto.

It is noted that the general method described herein for the formation of the salts of N-acyl-D-phenylalanines and alkyl esters of L-phenylalanine may be employed to afford the salts of the mirror images. Thus, contacting of an alkyl ester of DL-phenylalanine with an N-acyl-L-phenylalanine affords the salt comprised of N-acyl-L-phenylalanine and the alkyl ester of D-phenylalanine. The salt can be decomposed by usual methods to obtain pure alkyl ester of D-phenylalanine. That material may be hydrolyzed and acylated to provide resolving agent for use in the instant process. Typically, DL-phenylalanine methyl ester is contacted with N-acetyl-L-phenylalanine to afford the salt of D-phenylalanine methyl ester and N-acetyl-L-phenylalanine.

Depending on the availability of starting materials, various other methods of their preparation may be utilized. For example, DL-phenylalanine may be converted into the N-acyl-DL-phenylalanine with an appropriate acylating agent. Then that acylated derivative is contacted with an alkyl ester of L-phenylalanine to afford the salt of the N-acyl-D-phenylalanine and the alkyl ester of L-phenylalanine. Subsequent decomposition of the salt yields pure N-acyl-D-phenylalanine, useful as resolving agent. Alternatively, the alkyl ester of D-phenylalanine may be employed in a similar manner to yield N-acyl-L-phenylalanine, which, as noted hereinbefore, is useful to obtain the alkyl esters of D-phenylalanine from the corresponding DL-compounds. As mentioned previously the D-phenylalanine alkyl esters may be hydrolyzed and acylated to provide N-acyl-D-phenylalanine.

Particular examples further illustrating the present invention follow. They are, however, not intended to limit the invention either in spirit or in scope from that previously described and subsequently claimed. In the examples temperatures are presented in degrees Centigrade (° C) and quantities of materials in parts by weight unless parts by volume is specified.

EXAMPLE 1

N-Acetyl-D-phenylalanine

To a stirred solution of 20.0 parts of D-phenylalanine in 121 parts of water, cooled to about 1°–2°, is added, portionwise, an aqueous 50% sodium hydroxide solution until pH 12 is reached. Then 37 parts of acetic anhydride is added, while continuously adding aqueous 50% sodium hydroxide to keep the pH at about 12 and cooling the solution to keep the temperature at between about 10° to 30°. After about 20 minutes the mixture is acidified to pH 1 with concentrated hydrochloric acid and filtered. The recovered solid is recrystallized from water to afford N-acetyl-D-phenylalanine, melting at about 170°–172°.

EXAMPLE 2

N-Propionyl-D-phenylalanine

By substituting an equivalent quantity of propionic anhydride in the procedure of Example 1, there is produced N-propionyl-D-phenylalanine.

EXAMPLE 3

N-n-Butyryl-D-phenylalanine

Substitution of an equivalent quantity of butyric anhydride in the procedure of Example 1 affords N-n-butyryl-D-phenylalanine.

EXAMPLE 4

N-Acetyl-D-phenylalanine.L-phenylalanine Methyl Ester 10.35 Parts of N-acetyl-D-phenylalanine is dissolved in 40 parts of methanol, then treated with 17.9 parts of DL-phenylalanine methyl ester. A precipitate forms immediately and a additional 60 parts of methanol is added. The mixture then is filtered and the solid remaining is washed with additional methanol and dried. Recrystallization from methanol affords the crystalline salt of N-acetyl-D-phenylalanine and L-phenylalanine methyl ester, melting at about 170°–172° and displaying an $[\alpha]_D$ in 0.5% water of about −33.3°.

EXAMPLE 5

N-Acety-D-phenylalanine.L-Phenylalanine Methyl Ester

A solution consisting of 1.8 parts of L-phenylalanine methyl ester dissolved in 12 parts of methanol is treated, at room temperature, with 1.0 part of N-acetyl-D-phenylalanine. The precipitate which forms immediately is recovered by filtration and recrystallized from methanol to afford the crystalline salt of N-acetyl-D-phenylalanine and L-phenylalanine methyl ester, identical to the product obtained in Example 4, melting at about 170°–172°.

EXAMPLE 6

N-Acetyl-D-phenylalanine.L-Phenylalanine Ethyl Ester

Substitution of an equivalent quantity of DL-phenylalanine ethyl ester in the procedure of Example 4 and utilization of ethanol as solvent in place of the methanol described therein affords the salt of N-acetyl-D-phenylalanine and L-phenylalanine ethyl ester.

EXAMPLE 7

N-Propionyl-D-phenylalanine.L-Phenylalanine Methyl Ester

When an equivalent quantity of N-propionyl-D-phenylalanine is substituted in the procedure of Example 4, there is obtained the salt of N-propionyl-D-phenylalanine and L-phenylalanine methyl ester.

EXAMPLE 8

N-Acetyl-D-phenylalanine.L-Phenylalanine Methyl Ester

Utilization of water in place of methanol as the solvent in Example 4 affords the salt of N-acetyl-D-phenylalanine and L-phenylalanine methyl ester.

EXAMPLE 9

Hydrochloride Salt of L-Phenylalanine Methyl Ester 0.5 Part of the salt of N-acetyl-D-phenylalanine and L-phenylalanine methyl ester is dissolved in 5 parts of hot water. Then 0.2 part by volume of concentrated hydrochloric acid is added and the mixture is filtered, thereby collecting the N-acetyl-D-phenylalanine solid and leaving crude L-phenylalanine methyl ester hydrochloride in the filtrate. The filtrate is evaporated to dryness, and the hydrochloride salt of L-phenylalanine methyl ester then is dissolved in water. Sodium carbonate is added, then ether. The ethereal extract is separated and acidified to yield the hydrochloride salt of L-phenylalanine methyl ester, which, upon recrystallization from methanol, exhibits an $[\alpha]_D$ in 2% ethanol of about +35.7°.

EXAMPLE 10

Hydrochloride Salt of L-Phenylalanine Methyl Ester

A stirred solution of 2.0 parts of the salt of N-acetyl-D-phenylalanine and L-phenylalanine methyl ester in 20 parts of water is treated with 3.5 parts of potassium carbonate. An aqueous layer and an oily layer form and the mixture is extracted with ether. The aqueous layer, containing N-acetyl-D-phenylalanine, is separated and acidified with hydrochloric acid to yield, after cooling and filtering, N-acetyl-D-phenylalanine. The ethereal layer is dried over anhydrous sodium sulfate, then acidified with a hydrochloric acid-isopropanol mixture. The solid which forms is collected by filtration, then redissolved in methanol. Addition of ether affords crystals of the hydrochloride salt of L-phenylalanine methyl ester, displaying an $[\alpha]_D$ in 2% ethanol of about +35°. That product is the same as that obtained in Example 9.

EXAMPLE 11

By substituting equivalent quantities of the products of Examples 6 and 7 in the procedure of Example 10, there is afforded the hydrochloride salt of L-phenylalanine ethyl ester and the hydrochloride salt of L-phenylalanine methyl ester, respectively.

EXAMPLE 12

5.0 Parts of D-phenylalanine methyl ester, dissolved in 80 parts of methanol, is treated, at room temperature, with 0.90 part of sodium methoxide. The mixture is heated rapidly to reflux and maintained at reflux for about 2½ hours. Then the reaction mixture is cooled, acidified to pH 2 with concentrated hydrochloric acid and evaporated to dryness. The remaining crystalline residue is taken up in water, and sodium carbonate is added. 1,2-Dichloroethane is added to form two phases and the mixture is shaken and filtered. The organic layer is separated, washed with saturated sodium chloride solution, dried over anhydrous magnesium sulfate and filtered. The filtrate is acidified with hydrochloric acid, cooled and stripped of solvent. Trituration with ether of the material which remains after solvent removal and subsequent filtration yields DL-phenylalanine methyl ester hydrochloride, melting at about 162°.

EXAMPLE 13

Substitution of an equivalent quantity of D-phenylalanine ethyl ester in the procedure of Example 12 and utilization of sodium ethoxide and ethanol in place of sodium methoxide and methanol therein, affords DL-phenylalanine ethyl ester hydrochloride.

EXAMPLE 14

To 310 parts by volume of an aqueous 0.5N sodium hydroxide solution, heated to about 70°, is added, successively, 17.7 parts of N-acetyl-L-phenylalanine and 33.3 parts of DL-phenylalanine methyl ester hydrochloride. A precipitate forms and upon cooling and filtering, the salt of N-acetyl-L-phenylalanine and D-phenylalanine methyl ester is obtained. Recrystallization from hot water affords the pure salt exhibiting an $[\alpha]_D$ in 0.5% water of about +32.2°.

What is claimed is:

1. In a process for resolving alkyl esters of DL-phenylalanine, the step which comprises contacting a lower alkyl ester of DL-phenylalanine with N-(lower alkanoyl)-D-phenylalanine, wherein lower alkyl comprehends lower alkyl radicals having 1–4 carbon atoms inclusive and lower alkanoyl comprehends lower alkanoyl radicals having 1–8 carbon atoms inclusive.

2. As in claim 1, the step which comprises contacting the methyl estr of DL-phenylalanine with N-acetyl-D-phenylalanine.

3. As in claim 1 wherein the step of contacting a lower alkyl ester of DL-phenylalanine with N-acetyl-D-phenylalanine occurs in the presence of a polar solvent.

4. As in claim 1, the step which comprises contacting the methyl ester of DL-phenylalanine with N-acetyl-D-phenylalanine in methanol.

5. A composition of matter which comprises a salt of the formula

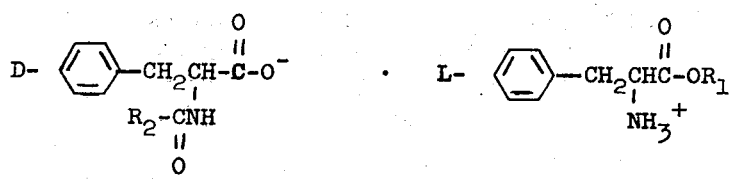

wherein $R_1$ is a lower alkyl radical having 1–4 carbon atoms inclusive and $R_2$ is hydrogen or a lower alkyl radical having 1–7 carbon atoms inclusive.

6. As in claim 5, a composition of matter of the formula

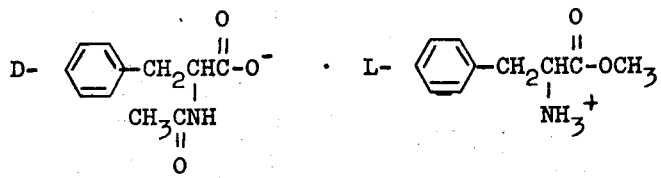

7. A process for resolving an alkyl ester of DL-phenylalanine which comprises contacting a lower alkyl ester of DL-phenylalanine with an N-(lower alkanoyl)-D-phenylalanine; isolating the salt of the lower alkyl ester of L-phenylalanine and the N-(lower alkanoyl)-D-phenylalanine; and separating the lower alkyl ester of L-phenylalanine from the N-(lower alkanoyl)-D-phenylalanine.

8. A process as in claim 7, wherein lower alkyl is methyl and lower alkanoyl is acetyl.

9. In a process for obtaining a lower alkyl ester of D-phenylalanine from the corresponding lower alkyl ester of DL-phenylalanine, the step which comprises contacting a lower alkyl ester of DL-phenylalanine with N-(lower alkanoyl)-L-phenylalanine, wherein lower alkyl comprehends lower alkyl radicals having 1–4 carbon atoms inclusive and lower alkanoyl comprehends lower alkanoyl radicals having 1–8 carbon atoms inclusive.

10. As in claim 9, the step which comprises contacting DL-phenylalanine methyl ester with N-acetyl-L-phenylalanine.

* * * * *